United States Patent [19]
Schwartz et al.

[11] Patent Number: 6,149,931
[45] Date of Patent: Nov. 21, 2000

[54] METHODS AND PHARMACEUTICAL COMPOSITIONS FOR THE CLOSURE OF RETINAL BREAKS

[75] Inventors: Daniel M. Schwartz, San Francisco, Calif.; Jeffrey A. Hubbell, Zumikon, Switzerland; Alexander R. Irvine, San Francisco, Calif.

[73] Assignees: The Regents of the University of California, Oakland; California Institute of Technology, Pasadena, both of Calif.

[21] Appl. No.: 09/181,041

[22] Filed: Oct. 27, 1998

Related U.S. Application Data

[60] Provisional application No. 60/063,297, Oct. 27, 1997.
[51] Int. Cl.[7] .................. A61F 2/14; A61K 13/02; A61K 47/30
[52] U.S. Cl. .................. 424/427; 424/443; 514/772.3
[58] Field of Search .................. 424/427, 443; 514/772.3

[56] References Cited

U.S. PATENT DOCUMENTS

| | | |
|---|---|---|
| 5,410,016 | 4/1995 | Hubbell . |
| 5,614,587 | 3/1997 | Rhee . |
| 5,626,863 | 5/1997 | Hubbell . |
| 5,801,033 | 9/1998 | Hubbell . |
| 5,820,882 | 10/1998 | Hubbell . |

OTHER PUBLICATIONS

Abrams et al., *Am J. Ophthalmol* 94:165–171 (1982).
Bloch et al., *Am J Ophthalmol* 71:666–673 (1971).
Burke et al., *Arch Ophthalmol* 105:404–408 (1987).
Charles, S., *Vitreous Microsurgery*, Williams & Wilkins, Baltimore, MD, 1987, p 135.
Cruise et al., *Biomaterials* 19:1287–1294 (1998).
de Juan et al., *Am J Ophthalmol* 99:272–274 (1985).
Dust et al., *Macromolecules* 23:3743–3746 (1990).
Federman et al., *Ophthalmol* 95:870–876 (1988).
Fineberg et al., *Am J Ophthalmol* 79:67–76 (1975).
Foulks et al., *Arch Ophthalmol* 105:256–259 (1987).
Gonvers M, *Ophthalmologica* 184:210–218 (1982).
Hida et al., *Am J Ophthalmol* 103:782–789 (1987).
Hida et al., *Retina* 8:148–153 (1988).
Hill–West et al., *Obstet Gynecol* 83:59–64 (1994).
Hill–West et al., *Proc. Natl. Acad. Sci. USA* (1994) 91:5967–5971.
Jeon et al., *Journal of Colloid and Interface Science* 142:149–158 (1991).
Jeong et al., *Nature* (1997) 388:860–862.
Laqua et al., *Am J Ophthalmol* 80:913–929 (1975).
Lean et al., *Trans Ophthalmol Soc* (UK) 102:203–205 (1982).
Lewen et al., *Arch Ophthalmol* 105:1212–1214 (1987).
Lewis et al., *Am J Ophthalmol* 103:672–680 (1987).
Machemer R., *Brit J Ophthalmol* 62:737–747 (1978).
McCuen et al., *Am J Ophthalmol* 102:199–207 (1986).
Michaels et al., *Retinal Detachment*, Klein EA, Ed. CV Mosby Co., St. Louis, MO, 1990, pp. 440, 847, 890–892.
Norton et al., *Am J Ophthalmol* 68:1011–1021 (1969).
Norton et al., *Trans Am Acad Ophthalmol Otolaryngol* 77:85–98 (1973).
Pathak et al., *J. Am. Chem. Soc.* 114:8311–8312 (1992).
Petersen J., *Graefe's Arch Clin Exp Ophthalmol* 225:452–456 (1987).
Sawhney et al., *Macromolecules* (1993) 26:581–587.
Sternberg et al., *Arch Ophthalmol* 103:90–94 (1985).
Tezuka et al., *Macromolecules* 26:575–580 (1993).
West et al., *Proc Natl Acad Sci* (*USA*) 93:13188–13193 (1986).
Yoon et al., *Ophthalmol* 95:1385–1388 (1988).

*Primary Examiner*—Carlos A. Azpuru
*Attorney, Agent, or Firm*—Cooley Godward LLP

[57] ABSTRACT

Described are compositions, methods, and articles of manufacture for the closure of retinal breaks with a non-toxic polymer. Transformation to a gel-like coat is achieved by photochemical reactivity, chemical reactivity, and by physicochemical response.

53 Claims, No Drawings

METHODS AND PHARMACEUTICAL COMPOSITIONS FOR THE CLOSURE OF RETINAL BREAKS

CROSS-REFERENCE TO RELATED APPLICATIONS

This application claims the benefit of the filing date of U.S. Patent Provisional Application Serial No. 60/063,297, filed Oct. 27, 1997, which is incorporated herein by reference.

ACKNOWLEDGEMENTS

This invention was supported in part by grants from 1-R43-EY12332. The U.S. Government may have rights in this invention.

INTRODUCTION

1. Technical Field

The present invention relates to methods and pharmaceutical compositions involving the use of polymers for the closure of retinal breaks.

2. Background

Successful management of rhegmatogenous retinal detachment is predicated upon closure of all retinal breaks. A rhegmatogenous retinal detachment occurs when vitreous fluid passes through a hole in the retina and the retina separates from the retinal pigment epithelium. When retinal detachment is treated with vitrectomy, closure of retinal breaks generally requires creation of a chorioretinal adhesion around each break (Michels et al., *Retinal Detachment*, Klein E A, Ed. CV Mosby Co., St. Louis, Mo., 1990, pp 440, 847, 890–892). These adhesive lesions are generated with either laser photocoagulation or cryotherapy. Maximal chorioretinal adhesion is ordinarily achieved within 2 weeks following treatment (Bloch et al., *Am J Opthalmol* 71:666–673 (1971); Yoon et al., *Ophthalmol* 95:1385–1388 (1988)). To keep the retina in apposition with the retinal pigment epithelium during this time, prolonged intraocular tamponade with gas or silicone oil is utilized (Norton et al., *Am J Ophthalmol* 68:1011–1021 (1969); Norton et al., *Trans Am Acad Ophthalmol Otolaryngol* 77:85–98 (1973); Lean et al., *Trans Ophthalmol Soc* (UK) 102:203–205 (1982); Gonvers M, *Ophthalmologica* 184:210–218 (1982); Petersen J., *Graefe's Arch Clin Exp Ophthalmol* 225:452–456 (1987)).

When long acting gases such as $SF_6$ or $C_3F_8$ are used, patients often must keep their head in a face down position for 2 weeks after surgery (Michels et al., *Retinal Detachment*, Klein E A, Ed. CV Mosby Co., St. Louis, Mo., 1990, pp 890–892). This causes considerable discomfort in most patients, and not uncommonly, is the most difficult hurdle in post-operative management. Additionally, intraocular gas may be associated with a number of ocular complications including, cataract, glaucoma, corneal edema, and creation of retinal folds (Fineberg et al., *Am J Ophthalmol* 79:67–76 (1975); Abrams et al., *Am J Ophthalmol* 94:165–171 (1982); Foulks et al., *Arch Ophthalmol* 105:256–259 (1987); Lewen et al., *Arch Ophthalmol* 105:1212–1214 (1987)). Another potential disadvantage of gas as an intraocular tamponade is that by sequestering inflammatory factors between the bubble interface and the retina, it may promote scar tissue formation on the retinal surface (Charles, S., *Vitreous Microsurgery*, Williams & Wilkins, Baltimore, Md., 1987, p 135). As this scar tissue contracts, it can distort the retinal surface, and may cause re-detachment of the retina (proliferative vitreoretinopathy) (Machemer R., *Brit J Ophthalmol* 62:737–747 (1978); Laqua et al., *Am J Ophthalmol* 80:913–929 (1975)).

Using silicone oil as a post-operative intraocular tamponade has the advantage that the patient is not required to position face down for more than one day post-operatively. However, unlike gas, which is slowly reabsorbed into the blood stream, silicone must be surgically removed from the eye as a secondary procedure to prevent silicone induced ocular complications such as cataract, glaucoma, band keratopathy, corneal decompensation and promotion of proliferative vitreoretinopathy (PVR) (Federman et al., *Ophthalmol* 95:870–876 (1988); Sternberg et al., *Arch Ophthalmol* 102:90–94 (1985)).

Other less effective methods of retinal fixation to the underlying retinal pigment epithelium include retinal tacks (de Juan et al., *Am J Ophthalmol* 99:272–274 (1985); Burke et al., *Arch Ophthalmol* 105:404–408 (1987)), and cyanoacrylate glue (McCuen et al., *Am J Ophthalmol* 102:199–207 (1986)). Titanium or stainless steel metal retinal tacks have been used to attach the retina to the eye wall to treat giant retinal tears or after large relaxing retinotomies. The tacks do not create a confluent chorioretinal adhesion around the retinal tear and thus require supplemental laser or cryotherapy as well as intraocular tamponade with gas or silicone oil. Tacks are also associated with complications such as choroidal hemorrhage and dislodgment (Lewis et al., *Am J Ophthalmol* 103:672–680 (1987)).

Butyl-2-cyanocrylate glue has been used to close retinal breaks in animal models of experimental retinal detachment (McCuen et al; Hida et al., *Am J Ophthalmol* 103:782–789 (1987); Hida et al., 1988). The glue is applied directly to retinal holes, polymerizing rapidly to form a seal over the retinal hole. While successful at closing the break and creating a chorioretinal adhesion, some intraocular glues can cause local retinal toxicity, possibly from release of formaldehyde and cyanoacetate (Hida et al., 1987).

Patients suffering from retinal detachment are in need of a better method for temporarily closing retinal breaks while chorioretinal adhesions form, thus allowing recovery from surgery with a minimum of discomfort and/or ocular complications.

SUMMARY OF THE INVENTION

The present invention is directed to compositions, methods, and articles of manufacture for the closure of retinal breaks by applying a polymer formulation to the retinal surface in the vicinity of the retinal break. The invention provides methods for closing a retinal break in a mammal, comprising applying to the retinal surface over and around the retinal break a non-toxic polymer formulation comprising at least one polymer precursor, and transforming the polymer formulation into a gel-like coat. In a preferred embodiment, the polymer formulation comprises a photochemically reactive polymer precursor species that can be transformed from a liquid to gel form by exposure to light. Another preferred composition includes a mixture of two mutually reactive polymer precursors.

The invention also provides methods for the management of retinal detachment, comprising replacing the vitreous with gas, creating a chorioretinal adhesion around a retinal break, applying to the retinal surface over and around the retinal break a non-toxic polymer formulation comprising at least one polymer precursor, and transforming the polymer into a gel-like coat.

Also provided are methods for preventing proliferative vitreoretinopathy, comprising applying a non-toxic polymer formulation over and around the retinal break and extending beyond the break by a substantial amount, preferably to cover more than 75% of the retina.

In addition, the invention provides pharmaceutical compositions, methods for preparing such pharmaceutical compositions, and articles for manufacture for use in the methods described above.

DESCRIPTION OF SPECIFIC EMBODIMENTS

This invention pertains to the field of retinal surgery, particularly to the closure of retinal breaks. The invention provides a superior alternative to silicone oil or intraocular gas for post-operative tamponade. The methods of the invention comprise the application of a polymer formulation to the retinal surface over and around the retinal break. More extensive applications of the polymer formulation to the retinal surface can prevent post operative scar tissue formation and recurrent retinal detachment (proliferative vitreoretinopathy). The polymer formulation is applied in liquid form, assuring conformity to irregular tissue surfaces. It is then transformed to a thin, gel-like coat by photopolymerization with a light source. Alternatively, a liquid polymer precursor that auto-polymerizes is applied over the break and adjacent retina. The polymerized gel is bound to the retina and retinal pigment epithelium, and resists displacement with overlying turbulent fluid flow. It is water permeable and allows diffusion of small molecules such as oxygen, glucose and other essential nutrients. While the polymer adheres to the retina, it closes the retinal hole, preventing fluid from passing into the subretinal space.

Before or after application of the polymer formulation to the retinal surface, laser photocoagulation or cryotherapy can be applied around the break to form a chorioretinal adhesion, which reaches adequate strength to prevent retinal detachment by about 10–14 days after surgery (Yoon et al.). Typically laser is applied around an extra-macular hole, but not around macular holes. During this time, the polymer slowly biodegrades, but remains in place long enough to maintain retinal attachment and allow the retinopexy adhesion to reach maturity. Because the polymer closes the hole, the vitreous cavity can be filled with balanced saline solution at the end of surgery and no additional intraocular tamponade is required with gas or silicone. Therefore, patients avoid the difficulty of post-operative positioning if gas is used and avoid a second procedure to remove silicone oil if it is used instead of gas. Furthermore, complications associated with gas or silicone oil are avoided.

In addition to obviating the need for gas or silicone tamponade, wider application of the polymer formulation beyond the retinal break, to a portion of or the entire retinal surface, has the added benefit of preventing post-operative scar tissue formation on the retinal surface, which can distort the retinal surface and reopen retinal breaks (proliferative vitreoretinopathy, PVR). This is due in part to the fact that larger molecules, including proteins and cells which cause proliferative vitreoretinopathy, cannot traverse or adhere to the polymer formulation, and thus will not bind to the underlying retina during the post-operative period (West et al., *Proc Natl Acad Sci (USA)* 93:13188–13193 (1986)).

One aspect of the invention is a method for closing a retinal break in an animal, comprising applying a non-toxic polymer formulation to the retinal surface of the animal over and around the retinal break, and transforming the polymer formulation into a gel-like coat. Preferably, the resultant gel-like coat comprises a biodegradable polymer. By "retinal break" is meant a hole, tear, or other abnormal opening in the retina (also known as the neurosensory retina). Retinal breaks can develop from several conditions, including, but not limited to, myopia, congenital defects, trauma, and cataract surgery. Preferably the animal is a laboratory animal or domesticated animal, is more preferably a mammal, and most preferably is a human. Suitable laboratory animals include mice, rats, rabbits, monkeys, apes and other research animals. Suitable domesticated animals include dogs, cats, cattle, horses, goats, sheep, pigs, mules, donkeys, and other animals in the service or company of man.

A key feature of the requirements for the materials to be used in closing retinal breaks is that they adhere to the retina over and around the break. One way to provide for this feature is to produce the material implant from a liquid polymer precursor applied directly on and around the site of the retinal defect. By "polymer" is meant a molecule formed by the union of two or more monomers. A "monomer" is a repeating structure unit within a polymer. "Polymerization" is the bonding of two or more monomers to produce a polymer. For example, polymerization of ethylene forms a polyethylene chain, or polymerization of a monomer X and a monomer Y can yield a polymer with the repeating subunit X-Y. It will be appreciated that polymers can also be formed by the polymerization of more than two monomers and that two or more monomers can be present in unequal ratios in the resultant polymer. By "polymer precursor" is meant a molecule that is subsequently linked by polymerization to form a polymer, which is larger than the polymer precursor. As discussed in greater detail below, polymerization can be achieved in various ways, such as by photopolymerization, autopolymerization, or physicochemical polymerization. The polymer precursor can itself be a polymer, such as, for example, poly(ethylene glycol). Alternatively, the polymer precursor can be a molecule other than a polymer, such as a protein, for example, albumin, collagen, gelatin, or other non-polymeric molecules.

The polymer precursor is usually present in the polymer formulation at a concentration in a range of about 0.01% to about 90%. The actual concentration varies with the polymer precursor used and its toxicology. Most polymer precursors are preferably used at a minimal concentration of about 5% because at lower concentrations it may be difficult to form a gel. However, by increasing the hydrophobicity of the ends of the polymer precursor, concentrations as low as about 1%, preferably about 3%, can be used to form a gel. High molecular weight precursors (i.e., greater than about 70,000 g/mol, preferably greater than about 100,000 g/mol), such as, for example, acrylated hyaluronic acid are preferably present at a concentration not greater than about 1%. See, for example, U.S. Pat. Nos. 5,801,033; 5,820,882; 5,626,863; and 5,614,587, incorporated herein by reference.

Transformation of the polymer precursor to a thin, gel-like coat can be accomplished in a number of ways, for example, by photochemical reactivity, by chemical reactivity, and by physicochemical response. When such a liquid-to-solid transition occurs directly upon the tissue surface, via any of the approaches described above, the resulting biomaterial implant adheres to the tissue surface. Liquid polymer precursor is applied over and around the retinal break, covering the breached area of the retina and overlapping the unbreached area of the retina by an amount sufficient to maintain adhesion of the polymerized implant to the retinal surface. Typically, the polymerized implant extends over the unbreached area of the retina by about 0.1 mm to about 5 mm, and can extend over a substantial portion of the retinal surface if desired, up to the entire retinal surface. Preferably the polymerized implant extends over the unbreached area of the retina by about 0.5 mm to about 2 mm.

The transformation of polymer precursor into a gel-like coat can be achieved by photopolymerization of the polymer formulation. Photochemically activatable polymer precursors suitable for the methods of the invention include precursors comprising a water-soluble polymer as the central domain, such as, for example, poly(ethylene glycol) (PEG)-based polymers. PEG is a polymer of the formula $HOCH_2(CH_2OCH_2)_nCH_2OH$, wherein n is an integer giving rise to molecules ranging in molecular weight typically from about 200 g/mol to greater than about 75,000 g/mol, preferably between about 6,000 g/mol to about 35,000 g/mol. Some specific PEG molecules have a molecular weight of about 400, 1350, 3350, 4000, 6000, 8000, 18500, 20000, or 35000. PEG molecules having a molecular weight not specifically listed, but nonetheless within a range of about 200 g/mol to greater than about 75,000 g/mol are also contemplated. Lower molecular weight PEG formulations are referred to as short chain PEG formulations and typically have a molecular weight of about 4,000 g/mole or less. Higher molecular weight PEG formulations are referred to as long chain PEG formulations and have a molecular weight of greater than about 4,000 g/mol, preferably greater than about 8,000 g/mol, and can be greater than about 10,000 g/mol, and greater than about 20,000 g/mol. Preferably the long chain PEG formulations have a molecular weight in the range of about 7,000 g/mol to about 20,000 g/mol, with about 8,000 g/mol to about 10,000 g/mol being most preferred. One of ordinary skill in the art expects PEG molecules to be present in a distribution centered around the stated molecular weight, commonly as much as plus or minus about 20% of the stated molecular weight. Vendors often list the molecular weight of a PEG product as an average molecular weight (See, for example, the Sigma catalog).

Preferably the polymer precursors of the invention comprise reactive termini to allow for photopolymerization, such as, for example, free radical polymerizable termini. Examples of such reactive termini include acrylates and methacrylates, with acrylates being more preferred. Preferably the polymer precursor is a PEG diacrylate or tetracrylate.

Preferably the polymer precursor also comprises degradable regions of a molecular weight, relative to that of the water-soluble central domain, to be sufficiently small that the properties of the polymer precursor in solution, and the gel properties, are determined primarily by the central water-soluble chain. Typically the polymer precursor comprises about 0% to about 20%, preferably about 1% to about 10%, degradable regions. Examples of such degradable regions include, but are not limited to, hydrolytically labile oligomeric extensions, such as, for example, poly(α-hydroxy esters). Examples of poly(α-hydroxy esters) include poly(dl-lactic acid) (PLA), poly(glycolic acid) (PGA), poly (3-hydroxybutyric acid) (HBA), and polymers of ε-caprolactone. The hydrolytic susceptibility of some of the ester linkages is in the following order: glycolidyl>lactoyl>ε-caprolactyl.

In a preferred embodiment, the polymer precursor has the formula:

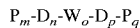

$P_m\text{-}D_n\text{-}W_o\text{-}D_p\text{-}P_q$ wherein W is a water-soluble polymer; D is a degradable moiety; P is a photopolymerizable moiety; m and q are integers from 1 to about 10; o is an integer from 1 to about 100; and n and p are integers from 0 to about 120. W can be a linear polymer or a branched polymer. One of ordinary skill in the art would understand the formula provided above to include branched polymers having more than two termini and having degradable and/or photopolymerizable moieties on some or all of the termini of the branched polymer. A "degradable moiety" is an oligomeric compound that when integrated into a polymer precursor, creates within the polymer precursor a degradable region as described above. A "photopolymerizable moiety" is a moiety that allows the polymer precursor to polymerize upon exposure to light. Some wavelengths suitable for catalyzing polymerization are discussed in more detail below.

Typically, the values of m and q are varied so as to achieve the desired degree of cross-linking and rate of transition from liquid-to-gel upon polymerization. The values of n and p are varied so as to achieve a desirable percentage of the degradable moiety, preferably between about 0.1% to about 25% degradable moiety, with about 1% to about 10% being most preferred. One of ordinary skill in the art would know to vary the values for n and p according to the value of o and the molecular weight of W in order to achieve this goal. Preferably m and q are integers from 1 to about 5, n and p are integers from 0 to about 10, and o is an integer from 1 to about 40. Alternatively, the polymer formulation can comprise in varying molar ratios polymer precursors having differing values for m, n, o, p and q so as to achieve a desirable percentage of the degradable moiety upon polymerization. For example, if W is a water soluble polymer having a molecular weight of at least 4,000 g/mol and o=1, n and p are integers from 0 to about 60, more preferably from 0 to about 25, even more preferably 1 to about 15, with 1 to about 5 being most preferred. Preferably W is a PEG molecule having a molecular weight from about 200 g/mol to about 75,000 g/mol. Preferably, if W is a PEG molecule having a molecular weight greater than 4,000, o is an integer from 1 to about 5, with 1 being most preferred.

Preferably the polymer precursor comprises a PEG central chain with degradable regions and photopolymerizable end groups that terminate the degradable regions. The polymer precursors of the invention can be synthesized by methods known in the art (Sawhney et al., *Macromolecules* (1993) 26:581–587; Hill-West et al., *Proc. Natl. Acad. Sci. USA* (1994) 91:5967–5971) and described herein in Examples 1–3.

A preferred polymer chain comprises lactic acid, glycolic acid or epsilon-caproic acid in the degradable region D. Incorporation of oligolactic acid into the polymer will increase its hydrophobic content. The polymer's hydrophobic content, and hence its strength of adhesion, varies directly with its % oligolactic, oligoglycolic, or oligoepsilon-caproic acid content. PEG is used to initiate the ring-opening polymerization of dl lactide, ll lactide, glycolide, or epsilon caprolactone to an extent such that from about 0.1% to about 25%, preferably about 1% or 10%, of the mass of the polymer chain is comprised of oligolactic acid, oligoglycolic acid, or oligoepsilon-caproic acid. This ratio is controlled via the reaction stoichiometry: the polymerization, if performed on dry polymer precursor, will produce very little lactic acid, glycolic acid, or epsilon-caproic acid homopolymer.

Biocompatibility of various biodegradable polymers can easily be assessed as described in Example 6 by injecting rabbits intravitreally with a polymer formulation, photopolymerizing the polymer precursor, and observing the animal clinically or histologically for signs of intraocular inflammation or toxicity.

The polymer precursors can be photopolymerized to form cross-linked networks directly upon the retinal surface. In addition to the polymer precursors, the biodegradable polymer formulation can also comprise reagents to facilitate the photopolymerization process, such as at least one photoinitiator, and one or more co-catalysts, such as, for example, N-vinylpyrrolidone and triethanolamine. Preferably a nontoxic photoinitiator such as eosin Y photoiniator is used. Other initiators include 2,2-dimethoxy-2-phenylacetophenone and ethyl eosin. The polymerization process can be catalyzed by light in a variety of ways, including UV polymerization with a low intensity lamp emitting at about 365 nM, visible laser polymerization with an argon ion laser emitting at about 514 nM, visible illumination from a conventional endoilluminator used in vitreous surgery, and most preferably by illuminating with a lamp that emits light at a wavelength between 400–600 nM, such as, for example, a 1-kW Xe arc lamp. Illumination occurs over about 1–120 seconds, preferably less than 30 seconds. Since the heat generated is low, photopolymerization can be carried out in direct contact with cells and tissues. Indeed, similar materials have been successfully utilized for the encapsulation of pancreatic islet cells and for the prevention of post-operative adhesion formation (Hill-West et al. *Obstet Gynecol* 83: 59–64 (1994).

Alternatively, the transformation of the polymer formulation into a gel-like coat can be achieved by autopolymerization of the polymer formulation. Auto-chemically reactive polymer gels may be formed by mixing two or more mutually reactive polymer precursors to result in a cross-linked polymer network. Usually, the polymer formulation comprises a first polymer precursor and a second polymer precursor, the first and second polymer precursors being mutually reactive. Preferably the first and second polymer precursors are present in about equimolar amounts. Typically, at least one of the reactive polymer precursors is a PEG based polymer precursor. Preferably, both polymer precursors are PEG based polymer precursors.

Suitable first polymer precursors include proteins, such as, for example, albumin, proteins derived from skin, connective tissue, or bone, such as collagen or gelatin, other fibrous proteins and other large proteins, tetra-amino PEG, copolymers of poly(N-vinyl pyrrolidone) containing an amino-containing co-monomer, aminated hyaluronic acid, other polysaccharides, and other amines. Preferably the tetra-amino PEG has a molecular weight of at least about 3,000 g/mol, preferably more than about 6,000 g/mole, even more preferably more than about 10,000 g/mol, and more preferably at least about 20,000 g/mol.

Suitable second polymer precursors include, but are not limited to, terminally-functionalized PEG, such as difunctionally activated forms of PEG. Some activating groups include epoxy groups, aldehydes, isocyanates, isothiocyanates, succinates, carbonates, propionates, etc. Examples of such forms of PEG include, but are not limited to, PEG di-succinimidyl glutarate (SG-PEG), PEG di-succinimidyl (S-PEG), PEG di-succinimidyl succinamide (SSA-PEG), PEG di-succinimidyl carbonate (SC-PEG), PEG di-propionaldehyde (A-PEG), PEG succinimidyl propionate, and PEG di-glycidyl ether (E-PEG) (U.S. Pat. No. 5,614,587) and other epoxy-derivatized PEG molecules, PEG nitrophenyl carbonate, PEG dialdehydes, PEG di-isocyanates, PEG di-isothiocyanates, and the like. Particularly preferred is a di-N-hydroxysuccinimidyl-activated dicarboxyl (PEG), such as a di-N-hydroxysuccinimidyl PEG. Other suitable difunctionally activated forms of PEG can be obtained from the Shearwater Polymers Catalog (see, for example, the "Electrophilically Activated" section of their website at http://www.swpolymers.com).

Preferred autochemically reactive polymer precursor pairs include (1) a tetra-amino PEG and a di-N-hydroxysuccinimidyl PEG; (2) a tetra-amino PEG and a di-succinimidyl carbonate PEG; (3) collagen, gelatin, or albumin and a di-N-hydroxysuccinimidyl PEG; (4) collagen, gelatin, or albumin and a di-succinimidyl carbonate PEG; and (5) other suitable autochemically reactive polymer pairs. Most preferred for the methods of the invention is the combination of a tetra-amino PEG and a di-N-hydroxysuccinimidyl PEG. If a di-N-hydroxysuccinimidyl active PEG is mixed with a di-amino PEG, a high molecular weight polymer results, but not a cross-linked hydrogel. However, if a di-N-hydroxysuccinimidyl activated PEG is mixed with a tetra-amino PEG, a cross-linked hydrogel network is formed, liberating only N-hydroxysuccinate as a reaction product. N-hydroxysuccinate is water-soluble and of very low toxicity. Preferably the di-N-hydroxysuccinimidyl PEG used in combination with a tetra-amino PEG is a di-N-hydroxysuccinimidyl activated succinate-terminated PEG. Di-N-hydroxy-succinimidyl activated glutarate-terminated PEG is less preferred because, when used in combination with a tetra-amino PEG, can produce ocular inflammation. These hydrogels can degrade by spontaneous hydrolysis at the linking group at the end of the polymer chain and can degrade within the protein backbone of a protein-containing gel. With gels formed from a PEG-containing first component and a PEG-containing second component, one can include a hydrolytically degradable oligolactic acid, oligoglycolic acid, or oligoepsilon-caproic acid domain, for example. Gels formed from protein-based, peptide-based, or polysaccharide-based precursors can also degrade under the enzymatic influences of the body.

Biocompatibility of various reactive polymer precursor pairs can easily be assessed as described in Example 7 by injecting a rabbit intravitreally with a mixture of the members of the polymer precursor pair, and observing the animal visually or histologically for signs of intraocular inflammation or toxicity.

The extent of incorporation into the gel phase can be optimized by manipulating various parameters, such as the pH of the reaction solution and the ratio of the first polymer precursor to the second polymer precursor. Typically, when PEG tetra-amine and di-N-hydroxy succinimidyl PEG are to be used, polymer precursors are separately reconstituted immediately before use in physiological saline at pH 8. They are mixed to yield a total final concentration of about 10% using an optimal ratio of molar amounts of each precursor, preferably equimolar. Given that reaction begins immediately after mixing, injection onto the retina is preferably performed immediately. The mixing is performed with two syringes and a connector. Alternatively, a syringe with two barrels can be used. Static mixture occurs on the tip of the syringe immediately before the polymer precursor solutions pass through a needle or cannula. The time between the initiation of mixing and injection is usually less than about 30 seconds. This can be achieved by positioning a 30 gauge cannula (or other suitable sized cannula, or a needle) attached to a syringe(s) containing polymer over the break prior to mixing the components.

Toward physicochemical transition, block copolymers of poly(ethylene glycol)—poly(propylene glycol)—poly(ethylene glycol), commonly referred to as Pluronics™, can be used to form polymer solutions that are liquid at 4° C. but gels at 37° C., permitting injection of the cold fluid with solidification to form a physicochemically cross-linked polymer network on the surface of the tissue. Other thermoreversible biocompatible biodegradable polymers are known. For example, Jeong et al., *Nature* (1997) 388:860–862, recently described copolymers of PEG and lactic acid that display favorable liquid-to-solid gelation transitions. Such materials can either be applied warm and fluid and allowed to cool in vivo into a gel form, or can be applied cool and fluid and allowed to warm in vivo into a gel form, depending upon the physicochemical characteristics of the gel and its precursor.

Polymers that display a physicochemical response to stimuli have been explored as potential drug-delivery systems. Stimuli studied to date include chemical substances and changes in temperature, pH and electric field. Homopolymers or copolymers of N-isopropylacrylamide and poly(eythlene oxide)-poly(propylene oxide)-poly (ethylene oxide) (known as poloxomers) are typical examples of thermosensitive polymers, but their use in drug delivery is problematic because they are toxic and non-biodegradable. Biodegradable polymers used for drug delivery to date have mostly been in the form of injectable microspheres or implant systems, which require complicated fabrication processes using organic solvents. Such systems have the disadvantage that the use of organic solvents can cause denaturation when protein drugs are to be encapsulated. Furthermore, the solid form requires surgical insertion, which often results in tissue irritation and damage. The methods of the invention involve the synthesis of a thermosensitive, biodegradable hydrogel consisting of polymer precursor blocks of poly(ethylene oxide) and poly(L-lactic acid). Aqueous solutions of these polymer precursors exhibit temperature-dependent reversible gel-sol transitions. By "sol" is meant a polymer precursor solution which is more liquid than solid. By "gel" is meant a polymer solution which is more solid than liquid. The hydrogel can be loaded in an aqueous phase at an elevated temperature (around 45 degrees C.), where they form a sol. In this form, the polymer is injectable. On subcutaneous injection and subsequent rapid cooling to body temperature, the loaded copolymer forms a gel.

The polymer formulations described above are applied in a manner consistent with the surgical procedure as a whole. Typically, the subretinal fluid is drained with fluid/gas exchange in order to flatten the retina. Laser photocoagulation or cryotherapy can then be performed around the break. The polymer formulation is then applied to the retinal surface as described above. Polymerization is effected as discussed above. Usually at least about 1 second to five minutes or longer is allowed to pass to ensure complete polymerization has occurred, and preferably the delay is less than 30 seconds. The gas is then removed and replaced with a balanced saline solution.

Another aspect of the invention is a method for management of retinal detachment in an animal, comprising applying a non-toxic, biodegradable polymer formulation to the retinal surface of the animal over and around the retinal break, and transforming the polymer formulation into a gel-like coat. As discussed above, closure of the retinal break prevents fluid from leaking into the potential space between the retina and the retina pigment epithelium. If desired, chorioretinal adhesions can be created, preferably by laser photocoagulation before or after application of the biodegradable polymer. A "chorioretinal adhesion" is an adhesion between the retina and underlying retinal pigment epithelium and choroid.

Yet another aspect of the invention is a method for the prevention of proliferative vitreoretinopathy (PVR), comprising applying a non-toxic, biodegradable polymer formulation more extensively to the retinal surface of an animal in need thereof than otherwise applied to close a retinal break. Preferably the polymer formulation is applied to at least about 25% of the retinal surface surrounding the retinal break, preferably to more than about 50% and applications to more than about 75% of the retinal surface to the entire retinal surface are most preferred. In a preferred embodiment, autopolymerizable polymer precursors are applied to the retinal surface as described above. In another preferred embodiment, a polymer precursor solution containing at least one photoinitiator is applied to the retinal surface around the retinal hole. Polymerization is then effected by any of the methods described above to close the retinal break. The eye is then filled with a solution containing at least one photoinitiator but no polymer precursor to coat the surface of the retina. Excess photoinitiator is drained from the eye. Next, polymer precursor solution that does not contain photoinitiator is applied to the remainder of the retinal surface and polymerization is again effected. The polymerization reaction results in a thin, transparent gel where the polymer precursor contacts the photoinitiator, but not in areas free of photoiniator. This results the formation of a gel only on the surface of the retina. The eye is once again filled with fluid. Unpolymerized precursors are then irrigated from the eye. The adherent polymer biodegrades over a 2–10 week period. The polymerized gel overlying the retina both closes the retinal break and prevents adherence of scar tissue that could cause proliferative vitreoretinopathy and recurrent retinal detachment. Another embodiment omits the initial step of applying a polymer precursor solution containing photoinitiator directly to the hole.

A further aspect of the invention is the use of at least one non-toxic, biodegradable polymer precursor for the preparation of a pharmaceutical composition for closing a retinal break in a mammal. Suitable polymer precursors and other components of the pharmaceutical composition are discussed in detail above in the sections describing the components of suitable polymer formulations. Additional components can include any other reagents that catalyze polymerization of the polymer precursor, pharmaceutically suitable delivery vehicles for ocular administration, such as for delivery to the interior of the eye, and any other pharmaceutically acceptable additives.

The invention also provides articles of manufacture for use in closing a retinal break in a mammal with a non-toxic biodegradable polymer. In one embodiment, the article of manufacture comprises a first container comprising a polymer precursor of the formula:

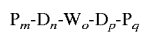

$P_m\text{-}D_n\text{-}W_o\text{-}D_p\text{-}P_q$ wherein W is a water-soluble polymer; D is a degradable moiety; P is a photopolymerizable moiety; m and q are integers from 1 to about 10; o is an integer from 1 to about 100; and n and p are integers from 0 to about 120. The first container can optionally contain at least one photoinitiator and can also optionally contain at least one co-catalyst. Where the first container does contain a photoinitiator in addition to the polymer precursor, the article of manufacture can optionally contain a second container comprising polymer precursor but no photoinitiator. The article of manufacture can optionally contain a third container comprising a photoinitiator solution but no polymer precursor. An article of manufacture comprising all three containers or just the second and third containers are useful for preventing PVR as described above. An article of manufacture comprising the first container only is sufficient for closing retinal breaks. The article of manufacture preferably further comprises instructions for use according to the methods described above involving photopolymerization.

In another embodiment, the article of manufacture comprises a first container comprising a first polymer precursor and a second container comprising a second polymer precursor, the first and second polymer precursors being mutually reactive. The first and second polymer precursors can be present in the container in admixture with a pharmaceutically suitable vehicle for delivery to the interior of the eye. Alternatively, any such vehicle can be added separately, if necessary, for example, to reconstitute the polymers. Suitable first and second polymer precursors are any of those polymer precursor pairs discussed above that can autopolymerize. Preferably the first polymer precursor is albumin, collagen or gelatin, and the second polymer precursor is a terminally-functionalized poly(ethylene glycol) (PEG). Typically, the first and second containers are separate syringes or are separate barrels of a single syringe having static mixture device at the tip of the syringe, and can also be vials or other cylindrical containers, such as, for example a segment of tubing. The article of manufacture can further comprise printed instructions for a method for closing a retinal break by combining the first and second polymer precursors immediately before applying to the retinal surface of the mammal over and around the retinal break. Usually, the first and second polymer precursors are combined by extruding from each container simultaneously into and through a connector onto the retinal surface. Suitable connectors are any structures that permit mixing of the first and second polymer precursors immediately before application to the retinal surface, such as, for example, a structure that is Y-shaped and comprises two tubular segments, each of which fits over an aperture in each container, and which are united into a single tubular segment.

The following examples illustrate, but in no way are intended to limit the present invention.

EXAMPLES

Example 1

Synthesis of 6 kD PEG Polymer Precursor

A PEG-co-poly(α-hydroxy acid) copolymer is synthesized. A total of 30 g of dry PEG 6K, 3.60 g of dl-lactide (5 mol dl-lactide/mol of PEG), and 15 mg of stannous octanoate are charged into a 100-mL round-bottomed flask under a nitrogen atmosphere. The reaction mixture is stirred under vacuum at 200° C. for 4 h and at 160° C. for 2 h and is subsequently cooled to room temperature. The resulting copolymer is dissoved in dichloromethane, precipitated in anhydrous ether, filtered, and dried. The α- and ω-hydroxyl end groups of PEGs with various molecular weights are used as ring-opening reagents to initiate the polymerization of either dl-lactide or glycolide to similarly form several other copolymers.

The copolymers are end-capped with acrylate groups to form a polymerizable polymer precursor. A total of 30 g of the intermediate copolymer is dissolved in 300 mL of dichloromethane in a 500-mL round-bottomed flask and is cooled to 0° C. in an ice bath. A total of 1.31 mL of triethylamine and 1.58 mL of acryloyl chloride are added to the flask, and the reaction mixture is sitrred for 12 h at 0° C. and 12 h at room temperature. The reaction mixture is filtered to remove triethanolamine hydrochloride, and the polymer precursor is obtained by pouring the filtrate in a large excess of dry diethyl ether. It is further purified by dissolution and reprecipitation once using dichloromethane and hexane, respectively. Finally, it is dried at 70° C. under vacuum for 1 day.

Example 2

Synthesis of 10,000-Da PEG Polymer Precursor

A macromolecular precursor is synthesized that consists of a central chain of poly(ethylene glycol) (PEG) with flanking regions of lactic acid oligomer and tetra-acrylate termini. The precursor is synthesized by dissolving 50 g of 10,000-Da PEG (Sigma) in toluene (Mallinckrodt, ACS grade) and refluxing under argon for 1 hour. 4.5 g of dl-lactide (Aldrich) and 50 $\mu$l of 50% (vol/vol) stannous octanoate (ICN) in toluene are added. The solution is refluxed under argon for 16 hours to achieve an average of five lactic acid groups per end, as estimated by proton NMR. The solution is cooled to about 20° C., and the polymer is precipitated with hexane (Mallinckrodt, ACS grade), filtered, washed, and dried. This polymer is dissolved in tetrahydrofuran (Mallinckrodt, ACS grade) under argon and cooled to about 15° C. 5.23 ml of triethylamine (Aldrich) and 3 ml of acryloyl chloride (Aldrich) are added to the mixture while bubbling argon through the solution. The mixture is then refluxed under argon for 24 hours. Triethylamine hydrochloride precipitate is removed by filtration. The macromolecular precursor is precipitated with hexane, filtered, washed, and dried. The precursor is stored at 0° C. under argon until use.

Example 3

Synthesis of PEG Diacrylates of Various Molecular Weights

PEG diacrylates of various molecular weights are synthesized as described in Cruise et al., *Biomaterials* 19:1287–1294 (1998). All solvents used in the synthesis are reagent grade or better and the reactants are used as received.

Fifty grams of PEG diol (Union Carbide) with a molecular weight of either 1350 (2K), 3350 (4K), 8000 (8K) or 20,000 (20K) were dissolved in 750 ml of benzene (Fisher) and water was removed by azeotropically distilling 250 ml of benzene. Triethylamine (Aldrich), in four fold molar excess based on PEG diol end groups, is added to the PEG solution at room temperature. Acryloyl chloride (Aldrich), in four fold molar excess based on PEG diol end groups, is added dropwise to the PEG solution to form acrylate diesters of PEG. The mixture is stirred overnight at 35° C. under argon. The insoluble triethylamine salts formed during the reaction are removed by filtration and the PEG diacrylate product is precipitated by the addition of 1.4 liters of diethyl ether (Fisher) chilled to 4° C. The PEG diacrylate precipitate is collected on a fritted funnel, redissolved in 100 ml of benzene, and reprecipitated with 1.4 liters of chilled diethyl ether twice more. The polymer is dried 24 h in a vacuum oven at 35° C.

PEG diacrylates are analyzed using nuclear magnetic resonance (NMR) spectroscopy and gel permeation chromatography (GPC). The degree of substitution of the PEG terminal alcohol for acrylate is determined using the NMR spectrum of PEG diacrylates and the method of Dust et al., *Macromolecules* 23:3743–3746 (1990), which compares the ratio of the integration from the PEG backbone (~3.5 ppm)

and the acrylate peaks (~5.8–6.4 ppm) to the known PEG weight average molecular weight. The extent of acrylation substitution is calculated using the following formula: % acrylation={PEG molecular weight}/{(integral of PEG backbone)/[(integral of acrylates)/6]/4X44}.

Example 4

Visible Laser Polymerization of 10,000-Da PEG Polymer Precursor

The tissue is incubated in 1 mM eosin Y (Sigma), a nontoxic photoinitiator, in Hepes-buffered saline (10 mM, pH 7.4) for 1 minute to adsorb the photoinitiator onto the surface of the tissue. The tissue is then rinsed twice in Hepes-buffered saline and infused with a 23% solution of the macromolecular precursor that also contains 100 mM triethanolamine (Aldrich) and 0.15% N-vinylpyrrolidone (Aldrich). The tissue is illuminated using an argon ion laser (514 nm, 70 mW/cm$^2$, 2-s exposure; American Laser, Salt Lake City) to convert the liquid precursor to a hydrogel on the surface of the tissue.

Example 5

Polymerization of 10,000-Da PEG Polymer Precursor with Emitted Light Between 400 and 600 nM The tissue is contacted with 1 mM eosin Y in Hepes-buffered saline, which is allowed to adsorb to the tissue for 1 minute. The eosin Y is withdrawn, and the tissue is rinsed twice with saline. The tissue is then contacted with a 23% solution of the precursor that also contains 100 mM triethanolamine and 0.15% N-vinylpyrrolidone. The tissue is then externally illuminated with a 1-kW Xe arc lamp that emits light between 400 and 600 nm (Optomed, Austin, Tex.) at an irradiance of 35 mW/cm$^2$. Illumination times are between 2 and 15 s.

Example 6

Assessing Biocompatibility of Photochemically Reactive Polymer Formulations Dutch Banded Rabbits are given general anesthesia with an intramuscular injection of xylazine and ketamine. Two Dutch Rabbits eyes are injected intravitreally with 100 μl of a mixture of a photochemically reactive polymer precursor, N-vinylpyrrolidone (1500 ppm), triethanolamine (20 mM), and eosin Y photoinitiator (10 μM) in a balanced saline solution. An external, hand-held Xenon arc light source (400–600 nm) is used to irradiate the globe of the eye for 1 minute.

The eyes are examined clinically with slit lamp and indirect ophthalmoscopy at days 1 and 5 post-injection for media opacity or other signs of ocular toxicity. Rabbits are then sacrificed on day 5 and the eyes are examined for histologic evidence of intraocular inflammation or toxicity.

Long Chain PEG (20,000 g/mol)

At days 1 and 5 post-injection of a polymer formulation containing 23% long chain PEG (20,000) g/mol), no media opacity or other signs of ocular toxicity were evident and the fundus was clearly visible in both eyes. The rabbits were sacrificed on day 5 and the eyes were processed for light microscopy. The animals showed no histologic evidence of intraocular inflammation or toxicity. The iridociliary processes showed none of the inflammatory processes evident in rabbit eyes injected with di-N-hydroxy succinimidyl activated glutarate-terminated PEG (Example 7). There was no fibrinoid reaction in the vitreous cavity. There was no inflammatory process evident in the retina or in the vitreous cavity.

Short Chain PEG (4,000 g/mol)

Rabbits were treated as described above, except that a retinal break was created as described below in Example 8. The animals were examined at 1 and 7 days after injection of a polymer formulation containing 23% short chain PEG (4,000 g/mol) by penlight and indirect ophthalmoscopy. Severe intraocular inflammation was evident in both treated eyes. A fibrinous pupillary membrane obscured the pupil of one eye and no view of the fundus was possible in either treated eye.

Example 7

Assessing Biocompatibility of Autochemically Reactive Polymer Formulations

Dutch Banded Rabbits are given general anesthesia with an intramuscular injection xylazine and ketamine. Autochemically reactive polymer precursors are mixed in a balanced saline solution and 100 μl is injected intravitreally using a 27 gauge needle on a tuberculin syringe. A gel is allowed to form.

The eyes are examined at days 1 and 5 for signs of intraocular inflammation and opacification of the ocular media. The rabbits are sacrificed on day 5 and the eyes are examined for histological evidence of intraocular inflammation or toxicity.

Di-N-hydroxysuccinimidyl Activated Glutarate-Terminated PEG

PEG tetra-amine (molecular weight 20,000 g/mol) and di-N-hydroxysuccinimidyl activated glutarate-terminated PEG (molecular weight 3,500 g/mol) were mixed to yield a polymer formulation containing 11.5% of each polymer precursor and injected intravitreally. At days 1 and 5 post-injection, severe intraocular inflammation and opacification of the ocular media were evident. The pupil was obscured and no view of the fundus was possible. The rabbits were sacrificed on day 5 and the eyes were processed for light microscopy. Both eyes showed marked inflammatory cell infiltration of the uveal tract and vitreous cavity. The iridociliary processes were haemmorhagic and edematous. A marked suppurative reaction with multiple eosinophilic polymorphonucleocytes was observed. A marked fibrinoid reaction was visible in the vitreous cavity. A subretinal inflammatory process was evident, with multiple eosinophilic polymorphonucleocytes that extended into the vitreous cavity. The inflammatory processes also extended into the anterior chamber.

Di-N-hydroxysuccinimidyl Activated Succinate-Terminated PEG

PEG tetra-amine (molecular weight 20,000 g/mol) and di-N-hydroxysuccinimidyl activated succinate-terminated PEG (molecular weight 3,500 g/mol) were mixed to yield a polymer formulation containing 11.5% of each polymer precursor and injected intravitreally. At days 1 and 5 post-injection, no media opacity or other signs of ocular toxicity were evident. The rabbits were sacrificed on day 5 and the eyes were processed for light microscopy. The rabbit eyes showed no histologic evidence of intraocular inflammation or toxicity. The iridocilliary processes showed none of the inflammatory processes evident in rabbit eyes injected with glutarate-terminated PEG as described above. There was no fibrinoid reaction in the vitreous cavity. There was no inflammatory process evident in the retina or in the vitreous cavity.

Example 8

Assessing Adherent Properties of Polymer Implant

Two New Zealand White Rabbits are given general anesthesia with an intramuscular injection of xylazine and ketamine. They are then pre-treated with cryotherapy behind the nasal and temporal limbus in the ora serrata region under direct visualization. Two weeks later, using sterile technique, the animals undergo vitrectomy and lensectomy. Endodiathermy is then used to create an approximate 1 disc diameter retinal break just superior to the medullary wing. Balanced saline solution is injected into the subretinal space using a 30 gauge cannula to create a localized retinal detachment. Fluid-gas exchange is then performed, and the retina is flattened. The polymer formulation is applied over the retinal break using a 30 gauge cannula. The fiberoptic endo-illuminator of the Premier Vitrector (Storz Instruments) is then used to irradiate the mixture for 1 minute, causing a thin, transparent polymerized gel to form over the retinal break. The eyes are then refilled with balanced saline solution. Attempts are made to displace the gel with the fiberoptic illuminator tip and the 30 gauge cannula.

Short Chain PEG

Short chain PEG diacrylate (molecular weight 4000 g/mol, ca. 10% concentration), N-vinylpyrrolidone (1500 ppm), and triethanolamine (20 mM) precursors were mixed with an eosin Y photoinitiator (10 $\mu$M) and applied over the retinal break. The polymer remained adherent to the hole and surrounding retina. Thus, it is possible to precisely apply the polymer precursor solution under gas, polymerize it with visible light, and form an adherent gel over the hole that resists mechanical displacement.

Example 9

Assessing Rate of Degradation of Polymer Implant

The duration of presence of non-toxic hydrogels on the retina is determined by incorporating commercially available 1 $\mu$M diameter fluorescence polymer beads (Polysciences) in the hydrogel precursor and thus in the hydrogel. This fluorescence can readily be observed in the eye non-invasively by the same type of fluorescence biomicroscopy commonly used to visualize the eyes of human patients given fluorescein. Eighteen Dutch Banded rabbits are given general anesthesia with an intramuscular injection of xylazine and ketamine. The right eyes are treated with cryotherapy behind the nasal and temporal limbus in the ora serrata region under direct visualization. Two weeks later, the animals are again given general anesthesia with an intramuscular injection of xylazine and ketamine. Lensectomy and vitrectomy are performed on the right eyes. A bent 30 gauge needle or vitrector is then used to create an approximately 1 disc diameter retinal break just superior to the medullary wing. Balanced saline solution is injected into the subretinal space using a 30 gauge cannula to create a localized retinal detachment. Fluid-gas exchange is then performed, and the retina is flattened. For example, the rabbits are divided into 3 groups of 6 rabbits each and given the treatments outlined below:

GROUP 1: 1% oligolactic acid photochemically reactive polymer

GROUP 2: 10% oligolactic acid photochemically reactive polymer

GROUP 3: Auto-chemically reactive polymer

All rabbits undergo vitrectomy, lensectomy, creation of a retinal break and detachment as described above. Fluid-gas exchange is then performed and laser photocoagulation applied around the retinal break in customary fashion. In each group of rabbits one of the hydrogel formulations and incorporated fluorescence polymer beads (Polysciences) is injected over and around the retinal break using a 30 gauge cannula. In the case of photochemical hydrogels, the fiberoptic endo-illuminator is used to irradiate the mixture for 1 minute to form an adherent gel overlying the retinal hole. The eyes are filled with balanced saline solution, sclerotomies and conjunctiva are closed, and a subconjunctival injection of gentamycin is given. On post-operative days 1, 3, 7, 14, 21, and 28 the rabbits are examined by fluorescence biomicroscopy to determine whether polymer remains adherent to the retina. Because a chorioretinal adhesion may take up to 2 weeks to reach maximal strength, polymer formulations should ideally remain adherent to the retina for at least this amount of time but not more than 4 weeks. The animals are sacrificed after 28 days and the eyes are examined histologically.

Example 10

Short-Term Retinal Break Closure with Polymer Formulation

Two New Zealand White Rabbits are given general anesthesia with an intramuscular injection of xylazine and ketamine. To prevent intraoperative bleeding, the animals are then euthanized with an intracardiac injection of Pentobarbital. The animals then immediately undergo vitrectomy and lensectomy. Endodiathermy is then used to create an approximate 1 disc diameter retinal break just superior to the medullary wing. Balanced saline solution is injected into the subretinal space using a 20 gauge cannula to create a localized retinal detachment. Fluid-gas exchange is then performed, and the retina is flattened. In one rabbit, balanced saline solution is then injected over the retinal break, which causes a localized retinal detachment. In the other rabbit, a photoreactive polymer formulation is applied over the retinal break using a 20 gauge cannula. The fiberoptic endo-illuminator of the Premier Vitrector (Storz Instruments) is then used to irradiate the mixture for 1 minute, causing a thin, transparent polymerized gel to form over the retinal break. Balanced saline solution is then injected over the polymer-covered retinal break.

PEG Diacrylate

PEG diacrylate (molecular weight 8,000 g/mol) containing 5% lactide was applied to a retinal break created as described above. Despite forceful injection of 3 cc of saline solution through a 20 gauge cannula, the retina remained attached.

Example 11

Assessing Ability of Polymer Implant to Seal Retinal Break

Twenty-four Dutch Banded rabbits are given general anesthesia with an intramuscular injection of xylazine and ketamine. The right eyes are treated with cryotherapy behind the nasal and temporal limbus in the ora serrata region under direct visualization. Two weeks later, the animals are again given general anesthesia with an intramuscular injection of xylazine and ketamine. Lensectomy and vitrectomy are performed on the right eyes. A bent 30 gauge needle or vitrector is then used to create an approximately 1 disc diameter retinal break just superior to the medullary wing. Balanced saline solution is injected into the subretinal space using a 30 gauge cannula to create a localized retinal detachment. Fluid-gas exchange is then performed, and the retina is flattened. For example, the rabbits are divided into 4 groups of 6 rabbits each and given the treatments outlined below:

GROUP 1: No polymer treatment
GROUP 2: 1% oligolactic acid photochemically reactive polymer
GROUP 3: 10% oligolactic acid photochemically reactive polymer
GROUP 4: Autochemically reactive polymer Rabbits in group 1 receive no polymer treatment. Rabbits in groups 2–4 receive one of the hydrogel formulations injected over and around the retinal break using a 30 gauge cannula. In the case of photochemical hydrogels, the fiberoptic endo-illuminator is used to irradiate the mixture for 1 minute to form an adherent gel overlying the retinal hole. Next, the eyes are filled with saline through the infusion port until the retinas of all control rabbits re-detach, which typically occurs after a few minutes of continuous infusion. Rabbits treated with polymer application to the retinal break are observed for re-detachment of the retina as they are infused with saline for 5 minutes. Since the goal is to assess the ability of the hydrogels to adhere to and close a retinal break, laser photocoagulation is not performed. The eyes are filled with balanced saline solution, sclerotomies and conjunctiva are closed, and a subconjunctival injection of gentamycin is given. Clinical examination with slit lamp and indirect ophthalmoscopy is performed on post-operative days 1, 3, 7, 14, 21, and 28. Evidence of retinal detachment, spontaneous retinal re-attachment, or signs of ocular inflammation is noted. At 28 days rabbits are sacrificed and the eyes are examined histologically for any evidence of toxicity of the procedure.

Example 12

Closure of a Retinal Break in a Human Patient with a Photoreactive Polymer Formulation A patient with rhegmatogenous retinal detachment requiring vitrectomy, such as retinal detachment with proliferative vitreoretinopathy or a detachment with a posterior retinal break, undergoes vitrectomy. Fluid-gas exchange with sterile air, $CO_2$, or xenon gas is performed to flatten the retina. Laser is applied around the hole if it is extra-macular. Laser is not applied around macular holes. 10–25% long chain PEG diacrylate (molecular weight 8,000 g/mol) containing about 5% lactide, N-vinyl pyrrolidone (1500 ppm), and triethanolamine (5 nM) are mixed with an eosin Y photoinitiator (1 mM) and applied to the retinal surface over and around the retinal hole under gas. Polymerization is then accomplished with 15–60 seconds of irradiation with either the fiberoptic endoilluminator or a xenon arc light source via a transpupillary route. The polymerization reaction results in a thin, transparent gel which closes the retinal break and remains adherent to the retinal surface. The eye is filled with a balanced saline solution. Over a 2–12 week period, preferably 2–3 weeks, the adherent polymer biodegrades. Thereafter, the retinal break is closed by a chorioretinal adhesion. No post-operative positioning is required.

Example 13

Closure of a Retinal Break in a Human Patient With an Autoreactive Polymer Formulation A patient with rhegmatogenous retinal detachment requiring vitrectomy, such as retinal detachment with proliferative vitreoretinopathy or a detachment with a posterior retinal break, undergoes vitrectomy. Fluid-gas exchange is performed to flatten the retina. Laser is applied around the hole if it is extra-macular. Laser is not applied around macular holes. Albumin and di-N-hydroxysuccinimidyl activated succinate-terminated PEG are applied simultaneously by mixing the contents of separate syringes through a connector to the retinal surface over and around the retinal hole under gas. The polymerization reaction begins immediately upon mixing and results in a thin, transparent gel which closes the retinal break and remains adherent to the retinal surface. The eye is filled with a balanced saline solution. Over a 2–12 week period, preferably 2–3 weeks, the adherent polymer biodegrades. Thereafter, the retinal break is closed by a chorioretinal adhesion. No post-operative positioning is required.

Example 14

Prevention of Proliferative Vitreoretinopathy (PVR)

Dutch Belted rabbits pre-treated with peripheral retinal cryotherapy undergo pars plana lensectomy and vitrectomy. A posterior retinal tear is then created with a bent 30 gauge needle or a vitrector. Balanced saline is then injected in the subretinal space to create a retinal detachment. Fluid-gas exchange is then performed and the retina flattened. Laser is applied around the hole(s) if it is extra-macular. Laser is not applied around macular holes. Then, a polymer precursor solution containing photoinitiator is applied to the retinal surface around the retinal hole. Polymerization is then accomplished with 15–60 seconds of irradiation with either the fiberoptic endoilluminator or a xenon arc light source via a transpupillary route, which closes the retinal break and remains adherent to the retinal surface.

The eye is then filled with photoinitiator to coat the surface of the retina. Excess photoinitiator is then drained from the eye. Next, polymer precursor solution that does not contain photoinitiator is applied to the remainder of the retinal surface and polymerization is again accomplished with 15–60 second of irradiation with either the fiberoptic endoilluminator or a xenon arc light source via a transpupillary route. The polymerization reaction results in a thin, transparent gel where the polymer precursor contacts the photoinitiator, but not in areas free of photoiniator. This results the formation of a gel only on the surface of the retina. The eye is once again filled with fluid. Unpolymerized precursors are then irrigated from the eye. Over a 2–10 week period the adherent polymer biodegrades. The polymerized gel overlying the retina both closes the retinal break and prevents adherence of scar tissue that could cause proliferative vitreoretinopathy and recurrent retinal detachment. No post-operative positioning is required.

Example 15

Prevention of Proliferative Vitreoretinopathy (PVR) in a Human Patient by Using a Photoreactive Polymer Formulation After Vitrectomy A patient with rhegmatogenous retinal detachment requiring vitrectomy, such as retinal detachment with proliferative vitreoretinopathy or a detachment with a posterior retinal break, undergoes vitrectomy. Fluid-gas exchange is performed to flatten the retina. Laser is applied around all retinal breaks. A solution containing 10 $\mu$M eosin Y photoinitator is then applied to the entire retinal surface covering all retinal breaks as well as intact retina. The photoinitiator solution is then washed from the vitreous cavity, but it remains adherent to the retinal surface. The vitreous cavity is then filled with a mixture of long chain PEG diacrylate (molecular weight 20,000 g/mol) containing about 10% lactide, N-vinyl pyrrolidone (1500 ppm), and triethanolamine (20 nM), which contacts the photoinitiator coated retina. The intraocular cavity is then irradiated for 15–120 seconds with a fiberoptic endoilluminator or a xenon arc light source via a transpupillary route to effect polymerization. The polymerization reaction results in a thin, transparent gel which closes the retinal breaks and remains adherent to the retinal surface. Coverage of the retinal tissue prevents cells and proteins that cause PVR from adhering to the retinal surface. The eye is irrigated with balanced saline solution to remove all unreacted polymer precursor. Balanced saline is left in the vitreous cavity and the patient has no positional requirement. Over a 2–16 week period, preferably 6–12 weeks, the adherent polymer biodegrades. Thereafter, the retinal break is closed by a chorioretinal adhesion. No post-operative positioning is required. The likelihood of PVR is reduced.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for closing a retinal break in a mammal, comprising:

applying over and around the retinal break a non-toxic polymer formulation comprising at least one polymer precursor that is a poly(ethylene glycol) (PEG) based polymer precursor, and transforming the polymer formulation into a gel-like coat.

2. The method of claim 1, wherein the transforming is by photopolymerization of the polymer precursor.

3. The method of claim 1, wherein the polymer formulation comprises a polymer precursor of the formula:

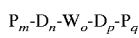

$P_m$-$D_n$-$W_o$-$D_p$-$P_q$ wherein W is a water-soluble polymer; D is a degradable moiety; P is a photopolymerizable moiety; m and q are integers from 1 to about 10; o is an integer from 1 to about 100; and n and p are integers from 0 to about 120.

4. The method of claim 1, wherein the PEG comprises reactive termini.

5. The method of claim 4, wherein the reactive termini are free radical polymerizable termini.

6. The method of claim 4, wherein the reactive termini are acrylate termini.

7. The method of claim 4, wherein the PEG comprises a long chain PEG having a molecular weight of at least about 8,000 g/mol.

8. The method of claim 4, wherein the PEG comprises a long chain PEG having a molecular weight of at least about 20,000 g/mol.

9. The method of claim 4, wherein the PEG based polymer precursor further comprises degradable regions.

10. The method of claim 9, wherein the degradable regions comprise from about 0.5% to about 20% oligolactic acid.

11. The method of claim 8, wherein the PEG based polymer precursor further comprises about 1% oligolactic acid.

12. The method of claim 8, wherein the PEG based polymer precursor further comprises about 10% oligolactic acid.

13. The method of claims 1 or 9, further comprising applying at least one photoinitiator to the retinal surface.

14. The method of claim 13, wherein the photoinitiator is an eosin Y photoinitiator.

15. The method of claim 13, wherein the formulation further comprises at least one co-catalyst.

16. The method of claim 10, wherein the formulation further comprises at least one photoinitiator and at least one co-catalyst.

17. The method of claim 10, wherein the formulation further comprises at least one photoinitiator, N-vinylpyrrolidone and triethanolamine.

18. The method of claim 1, wherein the transformation is by auto-polymerization of the polymer precursor.

19. The method of claim 1, wherein the polymer formulation comprises a first polymer precursor and a second polymer precursor, the first and second polymer precursors being mutually reactive.

20. The method of claim 19, wherein the first polymer precursor is an amine.

21. The method of claim 20, wherein the amine is a tetra-amino poly(ethylene glycol) (PEG).

22. The method of claim 19, wherein the first polymer precursor is a protein and the second polymer precursor is a terminally-functionalized poly(ethylene glycol)(PEG).

23. The method of claim 22, wherein the protein is albumin, collagen, or gelatin.

24. The method of claim 23, wherein the protein is albumin.

25. The method of claim 19, wherein the second PEG molecule is a di-N-hydroxysuccinimidyl PEG.

26. The method of claim 25, wherein the second polymer precursor is a hydroxysuccinimidyl activated succinate-terminated PEG.

27. The method of claim 25, wherein the second polymer precursor is a hydroxysuccinimidyl activated carbonate-terminated PEG.

28. The method of claim 1, wherein the mammal is a human.

29. The method of claim 1, wherein the gel-like coat comprises a biodegradable polymer.

30. The method of claim 1, wherein the polymer formulation is applied to more than about 50% of the retinal surface.

31. The method of claim 30, wherein the polymer formulation is applied to the entire retinal surface.

32. A method for management of retinal detachment in a mammal, comprising:

overlapping a retinal break with a non-toxic polymer formulation comprising at least one polymer precursor that is a poly(ethylene glycol) (PEG) based polymer precursor, and transforming the polymer formulation into a gel-like coat.

33. The method of claim 32, further comprising, prior to the overlapping, draining the subretinal fluid with fluid/gas exchange.

34. The method of claim 32, further comprising creating at least one chorioretinal adhesion around the retinal break.

35. The method of claim 32, wherein the chorioretinal adhesion is created before the polymer formulation is applied to the retinal surface.

36. The method of claim 32, wherein the chorioretinal adhesion is created by laser photocoagulation.

37. A method for preventing proliferative vitreoretinopathy in a mammalian eye having a retinal break, comprising:

(a) applying over and around the retinal break and to more than about 50% of the retinal surface of the mammal a first solution comprising a non-toxic polymer formulation comprising at least one polymer precursor that is a poly(ethylene glycol) (PEG) based polymer precursor, and (b) transforming the polymer formulation into a gel-like coat.

38. The method of claim 37, further comprising, prior to step (a), draining the subretinal fluid with fluid/gas exchange.

39. The method of claim 37, wherein the transforming is by photopolymerization of the polymer precursor.

40. The method of claim 37, wherein step (a) further comprises, prior to applying the first solution, the steps of (i) filling the eye with a second solution comprising at least one photoinitiator but no polymer precursor, and (ii) draining the eye, wherein the applying is by filling the eye with the first solution, wherein the first solution lacks a photoinitiator.

41. The method of claim 37, further comprising creating at least one chorioretinal adhesion around the retinal break.

42. The method of claim 40, further comprising, prior to the filling of the eye with the second solution, applying over and around the retinal break a third solution comprising polymer precursor and at least one photoinitiator.

43. A pharmaceutical composition for the closure of retinal breaks with a non-toxic, biodegradable polymer, comprising at least one photopolymerizable polymer precursor that is a poly(ethylene glycol) (PEG) based polymer precursor and at least one reagent that catalyzes photopolymerization of the precursor in admixture with a suitable vehicle for delivery to the interior of the eye.

44. The pharmaceutical composition of claim 43, wherein the polymer precursor is a poly(ethylene glycol) (PEG) based polymer precursor of the formula:

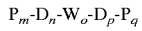

$P_m\text{-}D_n\text{-}W_o\text{-}D_p\text{-}P_q$ wherein W is a long chain PEG having a molecular weight of at least 8,000 g/mol; D is a degradable moiety; P is a photopolymerizable moiety; m and q are integers from 1 to about 10; o is an integer from 1 to about 100; and n and p are integers from 0 to about 120, and the reagents include at least one photoinitiator and at least one co-catalyst.

45. An article of manufacture for the closure of retinal breaks with a non-toxic polymer comprising a first container comprising poly(ethylene glycol) (PEG) based polymer precursor of the formula:

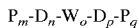

$P_m\text{-}D_n\text{-}W_o\text{-}D_p\text{-}P_q$ wherein W is a long chain PEG having a molecular weight of at least 8,000 g/mol; D is a degradable moiety; P is a photopolymerizable moiety; m and q are integers from 1 to about 10; o is an integer from 1 to about 100; and n and p are integers from 0 to about 120.

46. The article of manufacture of claim 45, further comprising a second container comprising a photoinitiator solution but no polymer precursor.

47. The article of manufacture of claim 45, further comprising printed instructions for closing a retinal break in a mammal, comprising applying the polymer precursor over and around the retinal break and transforming the polymer precursor into a gel-like coat.

48. The article of manufacture of claim 46, further comprising printed instructions for preventing proliferative vitreoretinopathy in a mammalian eye, comprising filling the eye with the contents of the second container, draining the eye, and filling the eye with the contents of the first container, wherein the first container does not contain a photoinitiator.

49. An article of manufacture for the closure of retinal breaks with a non-toxic polymer, comprising a first container comprising a first polymer precursor, a second container comprising a second polymer precursor that is a poly(ethylene glycol) (PEG) based polymer precursor, said first and second polymer precursors being mutually reactive.

50. The article of manufacture of claim 49, wherein the first polymer precursor is albumin, collagen or gelatin, and the second polymer precursor is a terminally-functionalized poly(ethylene glycol) (PEG).

51. The article of manufacture of claim 49, wherein the first and second containers are syringe barrels.

52. The article of manufacture of claim 49, further comprising printed instructions for a method for closing a retinal break in a mammal, comprising:

combining the first and second polymer precursors immediately before applying to the retinal surface of the mammal over and around the retinal break.

53. The article of manufacture of claim 52, wherein the combining occurs during extrusion into and through a connector connecting the first and second containers and onto the retinal surface.

* * * * *